(12) United States Patent
Tanioka et al.

(10) Patent No.: US 9,259,184 B2
(45) Date of Patent: Feb. 16, 2016

(54) PROBE FOR INSERTION INTO A LIVING BODY

(75) Inventors: Hiromichi Tanioka, Tokyo (JP); Toshinobu Ishida, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1776 days.

(21) Appl. No.: 12/412,831

(22) Filed: Mar. 27, 2009

(65) Prior Publication Data

US 2009/0247878 A1 Oct. 1, 2009

(30) Foreign Application Priority Data

Mar. 31, 2008 (JP) .................................. 2008-094011

(51) Int. Cl.
*A61B 5/00* (2006.01)

(52) U.S. Cl.
CPC .............. *A61B 5/6852* (2013.01); *A61B 5/0084* (2013.01); *A61B 5/0066* (2013.01)

(58) Field of Classification Search
USPC .................... 600/437, 439, 459, 462; 604/525
See application file for complete search history.

(56) References Cited

U.S. PATENT DOCUMENTS

| | | | |
|---|---|---|---|
| 5,125,895 A * | 6/1992 | Buchbinder et al. ........ | 604/95.01 |
| 5,199,417 A * | 4/1993 | Muller et al. ................. | 600/128 |
| 5,334,145 A * | 8/1994 | Lundquist et al. ......... | 604/95.04 |
| 5,531,719 A * | 7/1996 | Takahashi .................... | 604/525 |
| 5,876,331 A * | 3/1999 | Wu et al. ...................... | 600/139 |
| 6,638,222 B2 * | 10/2003 | Chandrasekaran et al. .. | 600/439 |
| 2003/0114901 A1 * | 6/2003 | Loeb et al. .................... | 607/89 |
| 2004/0064024 A1 * | 4/2004 | Sommer ....................... | 600/374 |
| 2005/0215942 A1 * | 9/2005 | Abrahamson et al. .......... | 604/22 |
| 2005/0222499 A1 * | 10/2005 | Banik et al. ................... | 600/132 |
| 2007/0088257 A1 * | 4/2007 | Fisher et al. ............. | 604/103.04 |
| 2007/0232893 A1 | 10/2007 | Tanioka | |

FOREIGN PATENT DOCUMENTS

| | | |
|---|---|---|
| JP | 58-108801 | 7/1983 |
| JP | 08-154940 | 6/1996 |
| JP | 9-070403 A | 3/1997 |
| JP | 2000-005181 | 11/2000 |
| JP | 2002-360578 | 12/2002 |
| JP | 2003-061963 A | 3/2003 |
| JP | 2004-081891 | 3/2004 |
| JP | 2004-275200 A | 10/2004 |
| JP | 2007-268133 A | 10/2007 |

* cited by examiner

*Primary Examiner* — Long V Le
*Assistant Examiner* — Ellsworth Weatherby
(74) *Attorney, Agent, or Firm* — Buchanan Ingersoll & Rooney PC

(57) ABSTRACT

A probe for insertion into a living body includes a sheath configured to be inserted into a living body, and a shaft positioned in the sheath. The shaft includes a tip portion configured to obtain diagnostic data at a distal portion thereof. The sheath includes a resin layer or a metal layer of at least one layer, and wherein the resin layer or the metal layer includes a spiral-shaped slit which is continuous from a distal portion to a proximal portion. The spiral-shaped slit includes a distal slit portion having the highest slit density, a middle slit portion which is continuous with the distal slit portion and which also has a lower slit density than the distal slit portion, and a proximal slit portion which is continuous with the middle slit portion and which also has a higher slit density than the middle slit portion.

18 Claims, 15 Drawing Sheets

PROBE FOR INSERTION INTO A LIVING BODY

This application is based on and claims priority to Japanese Patent Application 2008-094011 filed on Mar. 31, 2008, the entire content of which is hereby incorporated by reference.

TECHNOLOGICAL FIELD

The present invention generally relates to a probe for insertion into a living body. More specifically, the invention pertains to a probe insertable into a living body (e.g., a vessel such as a blood vessel) for executing display of an intraluminal cross-sectional image upon insertion into the living body.

BACKGROUND DISCUSSION

In the past, imaging diagnosis has been performed by inserting a probe having an imaging function into a blood vessel of a coronary artery of the heart or the like and a vessel of a bile duct or the like.

One type of imaging diagnostic apparatus is an intra vascular ultra sound (IVUS: Intra Vascular Ultra Sound) diagnostic apparatus. Generally, the intra vascular ultra sound diagnostic apparatus is constructed such that a probe equipped with an ultrasonic transducer is scanned radially in the blood vessel, a reflection wave (ultra sound echo) reflected by biological tissue in a coelom is received by the same ultrasonic transducer, and thereafter processes such as amplification, detection and the like are applied and a cross-section image of a blood vessel is visualized based on the strength of the generated ultra sound echo.

Another imaging diagnostic apparatus is an optical coherent tomography (OCT: Optical Coherence Tomography) diagnostic apparatus. An example of an optical coherent tomography diagnostic apparatus is disclosed in Japanese Unexamined Patent Publication No. 2007-268133. The optical coherent tomography diagnostic apparatus is an apparatus in which a probe equipped with an optical fiber which is mounted with a probe equipped with an optical lens and an optical mirror at the distal tip is inserted into a blood vessel, light is illuminated into the blood vessel while radially scanning the optical mirror arranged on the distal side of the optical fiber, and the cross-section image of the blood vessel is to be visualized based on the reflected light from the biological tissue. Further, there is proposed nowadays an imaging diagnostic apparatus which uses an optical frequency domain imaging (Optical Frequency Domain Imaging: OFDI) method which is referred to as a next generation OCT.

Japanese Unexamined Patent Publication No. 2004-275200 describes a catheter 1 in which the proximal side of a flexible tube 4 is held by a holding member H. The tube 4 in the vicinity of the holding member H includes a coil shaped reinforcement member 42 in the inside of the tube wall, and the proximal side of this coil shaped reinforcement member 42 is covered by a pipe-shaped reinforcement member 43. This pipe-shaped reinforcement member 43 is held on the holding member H.

Also, Japanese Unexamined Patent Publication No. 2003-61963 proposes an ultra sound catheter 1 provided with a built-in driving shaft 10 in a catheter sheath 2 which transmits a mechanical driving force from the hand side to the distal side of the catheter sheath 2 and with an ultra sound vibrator 13 connected to the distal side of the driving shaft 10. An X-ray opacity applying unit 12 is provided at least at a portion of the driving shaft 10. Paragraph [0021] of Japanese Unexamined Patent Publication No. 2003-61963 discloses that the catheter sheath 2 is formed, for example, by a multi-layer structure of resins such as polyimide, polyamide, polyester, polyethylene and polyurethane, and there is provided a reinforcement body of a metal-made knitted braid, a flat plate coil or the like between the resin layers on the proximal side from a position at which an intraluminal ultrasonic transducer can exist.

Also, Japanese Unexamined Patent Publication No. H09-070403, proposes an ultra sound catheter including an exterior shaft inserted into a coelom, a driving shaft inserted into the exterior shaft and transmitting a mechanical driving force from the proximal side to the distal side, and a housing provided with an ultrasonic transducer and fixed at the driving shaft so as to be positioned in the inside on the distal side of the exterior shaft and in which the driving shaft is an ultra sound catheter rotatable by an external driving source, wherein the exterior shaft includes a first elastic member of a coil shape at the distal portion, the housing includes a second elastic member extending to the distal side of the catheter at the distal portion, and the distal tip of the second elastic member is positioned in the first elastic member. Then, with respect to the main body portion of the exterior shaft, there is proposed a main body portion having a reinforcement layer positioned between the exterior and the interior layer and at the same time, the following matters are disclosed for the reinforcement layer.

At the distal portion of a tube which forms an intermediate layer (reinforcement layer) 102b (for example, elastic metal tube), there is provided a spiral shaped slit extending from the distal tip to the rear end side. Thus, the distal portion of the elastic metal tube forms a deformable portion which is flexible compared with other portions, so that with respect to the distal portion of the elastic metal tube, it is possible for the side wall thereof to be deformable toward the inside of the super-elastic metal tube. It is preferable for the slit to be formed to have widths gradually smaller from the distal tip toward the rear end side of the elastic metal tube, in other words, to have widths which become gradually larger toward the distal side. For this reason, the slit width at the distal tip of the elastic metal tube is formed to be maximum, and the more nearer the elastic metal tube is directed toward the distal tip, the more easily the deformation thereof occurs. It is preferable for the slit to be provided as many as around 2 to 8 pieces by being approximately equally spaced. It is preferable for the distal width of the slit (width of the maximum portion) to be around 0.05 mm to 0.5 mm. Also, it is preferable for the slit width to be approximately $1/6$ to $3/2$ of the outer diameter of the elastic metal tube and in particular, to be approximately $1/3$ to $1/1$ thereof. Also, with respect to the spiral shaped slit, it is also allowed for the pitch thereof to be short on the distal portion side of the slit and to be long on the proximal portion side of the slit. In a case in which the slit pitch changes, around 0.3 mm to 3.0 mm is preferable at the distal portion and around 5 mm to 10 mm is preferable at the proximal portion and in particular, at the middle portion between the distal portion and the proximal portion, it is preferable to have an intermediate pitch of the both sides or to have pitches gradually changing therebetween. Also, it is preferable for the slit 19 to have the changing pitches and the changing widths mentioned above.

SUMMARY

An imaging diagnostic apparatus using a probe executes continuous observation back and forth over the target lesion by inserting a probe, composed of a sheath and a shaft in the sheath for obtaining data, along a guide wire previously positioned at the target lesion and by moving the shaft to the proximal side in a state in which the sheath is inserted (so-called, pullback).

The probe for insertion into a living body used for the OCT, OFDI is constituted by a sheath and a shaft for obtaining data, and images are obtained by rotating the shaft for obtaining high-speed data in the sheath and by moving it to the proximal side while rotating it in a high-speed manner.

During this operation, a kinking phenomenon may occur at the proximal portion of the sheath when inserting the probe into the guiding catheter.

Upon studying this, the present inventors found that a sheath having well-balanced operationality can be formed by making the distal side relatively flexible and by employing the proximal side whose stiffness is relatively high, but with respect to the proximal portion if the stiffness becomes too high the operability of the probe upon insertion into the guiding catheter can result in kinking.

The probe disclosed here for insertion into a living body is composed of a sheath inserted into a living body and a shaft for obtaining data which is inserted into the sheath and at the same time which includes a tip portion for obtaining data for test subject diagnosis at the distal portion. The sheath exhibits excellent operationality at the proximal portion of the sheath, but is not as susceptible to kinking at the proximal portion.

A probe for insertion into a living body includes a sheath configured to be inserted into a living body, and a shaft configured to be positioned in the sheath. The shaft includes a tip portion configured to obtain diagnostic data at a distal portion thereof, wherein the sheath includes a resin layer or a metal layer of at least a one layer construction. The resin layer or the metal layer includes a spiral-shaped slit which is continuous from a distal portion to a proximal portion. The spiral-shaped slit includes a distal slit portion having the highest slit density, a middle slit portion which is continuous with the distal slit portion and which also has a lower slit density than the distal slit portion, and a proximal slit portion which is continuous with the middle slit portion and which also has higher slit density than the middle slit portion.

The middle slit portion includes a first middle slit portion which is continuous with the distal slit portion and which also has a lower slit density than the distal slit portion, and a second middle slit portion which is continuous with the first middle slit portion and which also has a lower slit density than the first middle slit portion. The proximal slit portion has a higher slit density than the second middle slit portion.

The slit density of the proximal slit portion is 5/4 to 5/2 times the slit density of the second middle slit portion.

The length of the proximal slit portion is 20 mm to 100 mm.

The sheath includes a kink inhibition member fixed at a portion at which the proximal portion of the proximal slit portion is positioned and whose diameter decreases toward the distal side of the sheath.

The distal portion of the proximal slit portion is positioned toward the distal side by 10 mm to 100 mm from the distal tip of the kink inhibition member.

The sheath includes a shaft lumen for housing the shaft for obtaining data and a guide wire lumen which is opened at the distal tip of the sheath and which extends toward the proximal side by a predetermined length.

The spiral-shaped slit includes a slit density transition portion of a predetermined length between the middle slit portion and the proximal slit portion in which the slit density becomes gradually high toward the proximal direction.

The spiral-shaped slit includes a slit density transition portion of a predetermined length between the distal slit portion and the middle slit portion in which the slit density becomes gradually low toward the proximal direction.

The spiral-shaped slit includes a slit density transition portion of a predetermined length between the first middle slit portion and the second middle slit portion in which the slit density becomes gradually lower toward the proximal direction.

The slit density of the spiral-shaped slit is varied by virtue of variations in the slit pitch length so that the longer the slit pitch becomes, the lower the slit density becomes.

The slit density of the slit is varied by virtue of variations in the slit width so that the shorter the slit width the lower the slit density.

The slit density of the spiral shaped slit is varied by virtue of variations in the length of the slit pitch and the slit width.

The shaft for obtaining data is a shaft including a drive-transmission hollow shaft and the tip portion for obtaining data which passes through the inside of the hollow shaft and also which is exposed from the distal portion of the hollow shaft, and is a shaft rotating by a rotation force applied at the proximal portion.

The shaft for obtaining data includes a drive-transmission hollow shaft, an optical fiber which passes through the inside of the hollow shaft and also which has the tip portion for obtaining data exposed from the distal portion of the hollow shaft and a connector connectable with a connection portion of an external drive apparatus, and the shaft rotates by a rotation force applied by the connector.

The shaft for obtaining data includes a drive-transmission hollow shaft, an ultrasonic transducer constituting the tip portion for obtaining data fixed at the distal portion of the hollow shaft and a connector connectable with a connection portion of an external drive apparatus, and a shaft rotating by a rotation force applied by the connector.

The probe for insertion into a living body disclosed here includes a sheath positionable in a coelom, wherein the sheath is comprised of a resin layer or a metal layer of at least one layer. This resin layer or metal layer includes a spiral shaped slit continuous from the distal portion to the proximal portion. The spiral-shaped slit includes a distal slit portion having the highest slit density, a middle slit portion continuous with the distal slit portion and also having lower slit density than the distal slit portion, and a proximal slit portion having higher slit density than this middle slit portion. In this manner, the sheath is provided with a portion which applies stiffness to the sheath and at the same time, in which the slit density composed of the distal slit portion and the middle slit portion becomes lower toward the proximal side and therefore, the distal side flexibility and the proximal side stiffness are provided, so that it exhibits excellent characteristics for being inserted into a living body and also, there is provided with a proximal slit portion which is continuous with the middle slit portion and also which has higher slit density than the middle slit portion. Therefore, there is included a proximal portion having flexibility to a certain degree, so that there is provided excellent operationality and at the same time, the occurrence of the kink at the proximal portion is rare.

DETAILED DESCRIPTION

Figure 1:
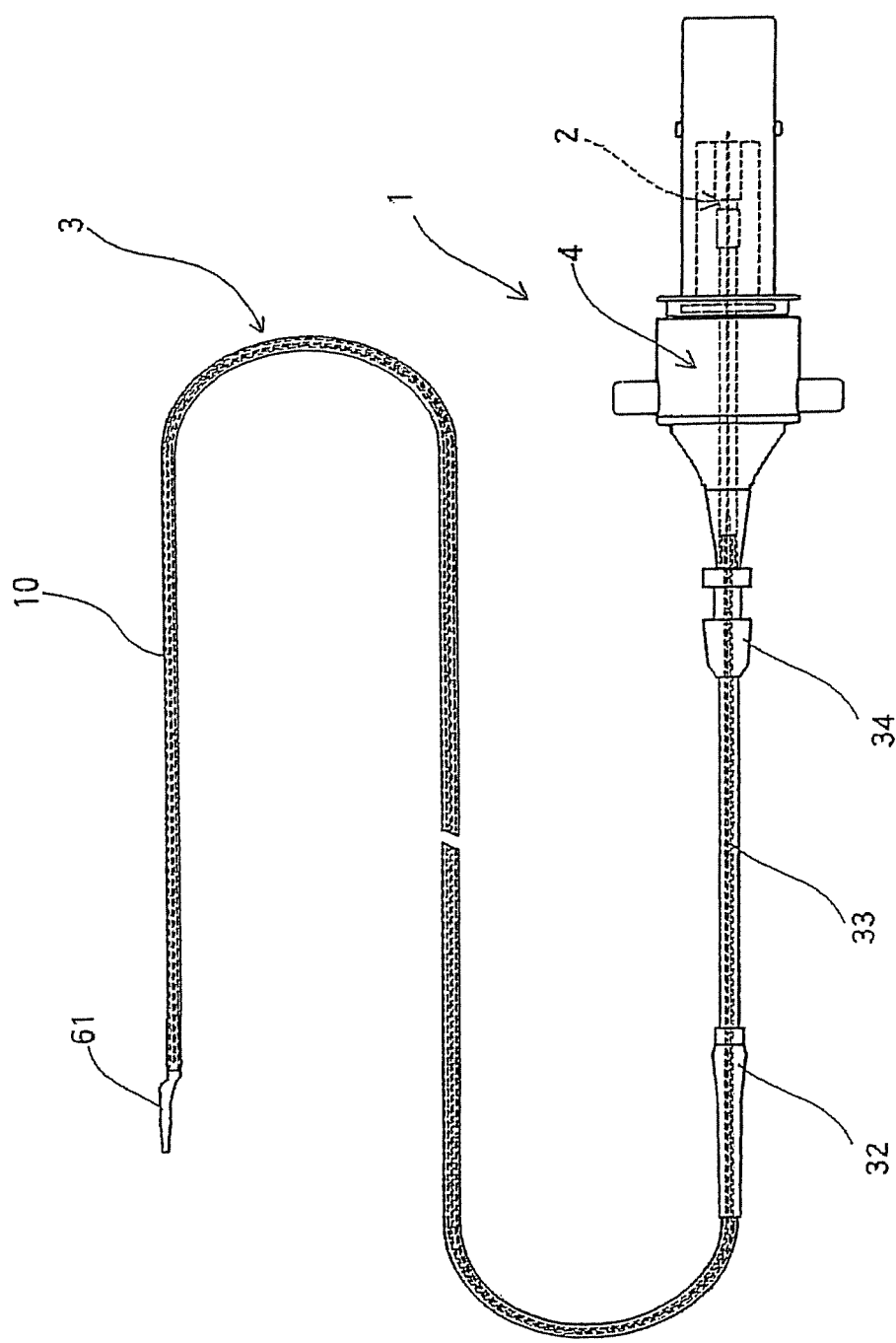
FIG. 1 is a plan view of a probe disclosed adapted to be inserted into a living body; in this embodiment the probe is an optical probe for insertion into a living body.
Figure 2:
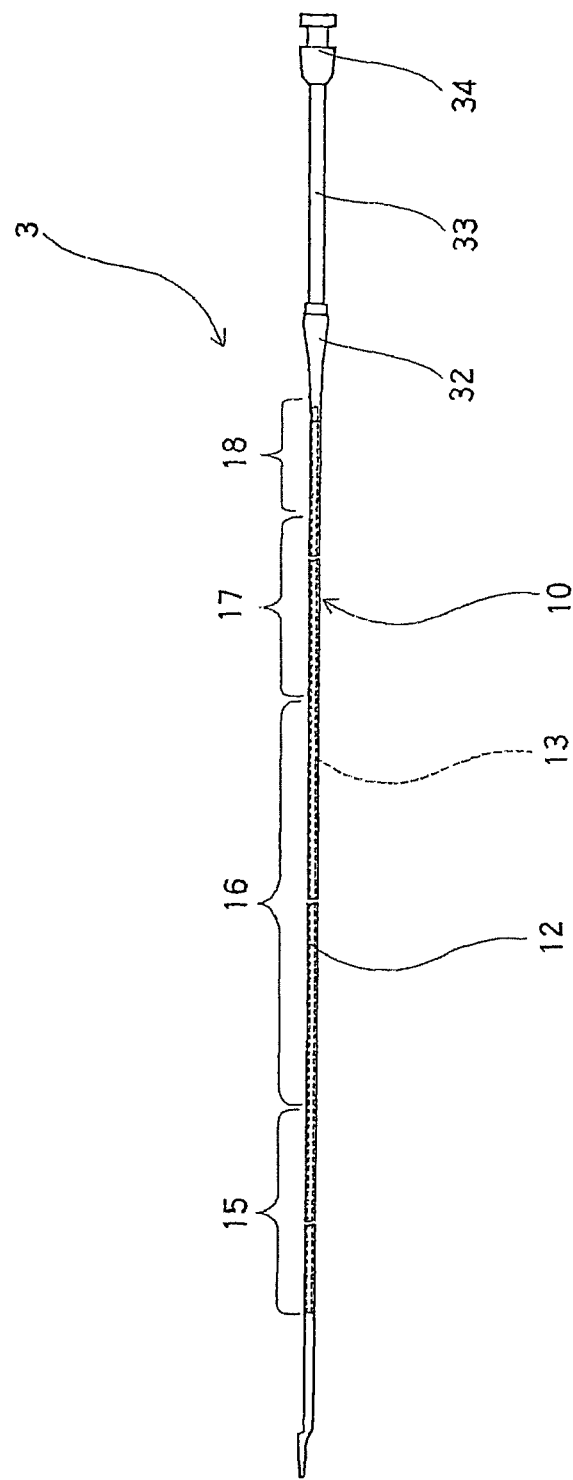
FIG. 2 is a plan view of one example of a sheath used for the probe.

Referring to FIG. 1, a probe for insertion into a living body 1 disclosed here is comprised of a sheath 3 inserted into a living body (specifically, into a coelom or the space in a living body where internal organs develop) and a shaft for obtaining data 2 which is inserted into, or positioned in, the sheath 3. The distal portion of the shaft 2 includes a distal tip portion 54 for obtaining data for test subject diagnosis (the distal tip portion 54 constitutes a device for obtaining data about the living body). The sheath 3 is composed of at least one layer that is a resin layer or a metal layer, with the resin layer or the metal layer including a spiral shaped slit 14, shown by way of example in FIG. 3, which extends continuously from a distal portion of the sheath to a proximal portion of the sheath. As illustrated in FIG. 2, the spiral-shaped slit 14 includes a distal slit portion 15 having the highest slit density, a middle slit portion 16, 17 which is continuous with the distal slit portion 15 and which has a lower slit density than the distal slit portion 15, and a proximal slit portion 18 which is continuous with the middle slit portion 17 and has a higher slit density than the middle slit portion 17.

The probe for insertion into a living body disclosed here has useful application as an optical probe for a diagnostic apparatus utilizing light, such as an optical coherent tomography diagnostic apparatus, an optical frequency domain imaging diagnostic apparatus and the like, and as an ultra sound probe for insertion into a living body.

The probe for insertion into a living body disclosed here will be explained with reference to an embodiment in which the probe is an optical probe for insertion into a living body.

This embodiment of the optical probe for insertion into a living body 1 is composed of the sheath 3 inserted into the coelom and the data-obtaining shaft 2 which is located in the sheath 3 and which is movable in the axial direction relative to the sheath over a predetermined distance during use. The data-obtaining shaft 2 includes a drive-transmission hollow shaft 22 and an optical fiber 21 having the tip portion 54 which passes through the inside of the hollow shaft 22 and also which is exposed beyond the distal portion of the hollow shaft 22. The shaft 2 is rotatable by application of a rotation force applied at the proximal portion of the shaft 2.

The optical probe for insertion into a living body 1 of this embodiment includes, in addition to the shaft for obtaining data 2 and the sheath 3 housing the shaft for obtaining data, an operation member 4 through which the shaft for obtaining data passes and also which is positioned on the proximal side from the sheath 3.

Figure 5:
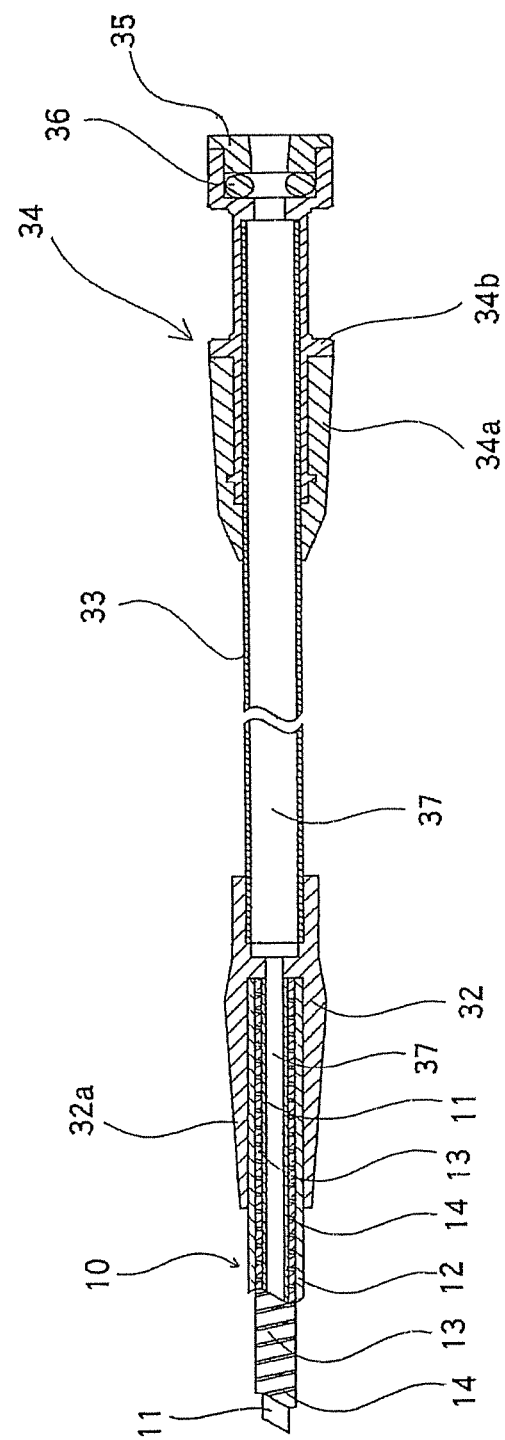
FIG. 5 is an enlarged cross-sectional view of a proximal portion of one example of a sheath used for the probe disclosed here.

As shown in FIG. 5, the sheath 3 is a tubular body including a shaft lumen 37 for housing the shaft 2 for obtaining data. The lumen extends from the proximal end in the distal direction. The sheath 3 also includes a guide wire lumen 63, depicted in FIG. 6, which opens at the distal tip of the sheath 3 and extends toward the proximal side over a predetermined length. In the illustrated embodiment, the opposite end of the guide wire lumen 63 is also open.

Referring to FIG. 2, in the probe for insertion into a living body 1 according to this embodiment, the sheath 3 includes a sheath tube 10, an anti-kink protector (kink inhibition member) 32 provided at a proximal end of the sheath tube 10, a distal sheath portion 61 provided at a distal tip of the sheath tube 10, a base portion tube 33 fixed at a proximal portion of the protector 32, and a tube hub 34 fixed at a proximal tip of the base portion tube 33.

The sheath tube 10 is constituted by an inside tube 11, an intermediate tube 13, and an outside tube 12. It should be noted that the sheath tube is not limited to a tube having this three-layer or three-tube structure, as it is also possible to employ a tube having a two-layer or two-tube construction.

The inside tube 11 is a tube body having the lumen 37 which extends from the proximal tip to the distal tip. The inner surface of the intermediate tube 13 is in close contact with the outer surface of the inside tube 11. The inner surface of the outside tube 12 is in close contact with the outer surface of the intermediate tube 13. The wall thickness of the inside tube 11 is preferably 30 μm to 300 μm, and preferably possesses a tensile breaking strength of at least 0.4 Kgf or more.

The distal tip of the inside tube 11 is positioned distally of the distal tip of the distal-most of the intermediate tube 13 and the outside tube 12, or is positioned distally of the distal tip of the intermediate tube 13 and the outside tube 12 by a predetermined length (distance). In other words, if the tubes 12, 13 are arranged so that one of them extends distally beyond the other, the distal tip of the inside tube 11 is positioned distally beyond the distal tip of the forward-most tube by the predetermined distance. On the other hand, if the tubes 12, 13 are positioned so that the distal tip of both tubes 12, 13 is located at the same position, the distal tip of the inside tube 11 is positioned distally beyond the distal tip of the tubes 12, 13 by the predetermined distance. By virtue of this construction, the distal end portion of the sheath tube 10 is comprised of only the inside tube 11. It is preferable for the aforementioned predetermined length or distance to be approximately 100 mm to 250 mm. It is also preferable for the outer diameter of the sheath tube 10 to be 0.5 mm to 1.5 mm, more preferably 0.8 mm to 1.0 mm. Also, it is preferable for the wall thickness of the outside tube to be approximately 0.05 mm to 0.2 mm.

The inside tube 11 can be fabricated of a synthetic resin. Examples of synthetic resins which can be used to manufacture the inside tube 11 include a light transmissive resin such as a fluoric resin of PTFE, ETFE or the like, polyimide, polyester (for example, polyethylene terephthalate, polybutylene terephthalate), polyolefin (for example, polyethylene, polypropylene), polyamide, polyimide and the like.

The outside tube 12 can also be fabricated of a synthetic resin. Examples of synthetic resins which can be used to manufacture the outside tube 12 include polyolefin (for example, polyethylene, polypropylene), polyolefin elastomer (for example, polyethylene elastomer, polypropylene elastomer, elastomer using ethylene-propylene copolymers or the like and the like), polyvinyl chloride, ethylene-vinylacetate copolymers, polyamide elastomer, polyurethane, a thermoplastic resin of a fluoric resin or the like, silicon rubber or the like. Preferably, polyethylene, polyamide elastomer or polyurethane is used. It is preferable for the outside tube 12 to be of sufficient flexibility that it does not disturb the curvature of the inner tube.

The intermediate tube 13 is a tube body having a lumen which passes-through from the proximal tip to the distal tip. It is preferable for the material forming the intermediate tube 13 to be harder than the forming materials of the inside tube 11 and the outside tube 12. The intermediate tube 13 can be, for example, a metal tube, a hard synthetic resin tube or the like. It is preferable for the metal tube to be a tube body such as a stainless-steel (SUS304, SUS316 or the like), a super-elastic metal and the like. Also, examples of materials which can be sued to fabricate the hard synthetic resin tube include a hard resin such as a fluoric resin of PTFE, ETFE or the like, polyimide, polyester (for example, polyethylene terephthalate, polybutylene terephthalate), polyolefin (for example, polyethylene, polypropylene), polyamide, polyimide and the like. The wall thickness of the intermediate tube 13 is preferably approximately 0.05 mm to 0.2 mm.

Figure 3:
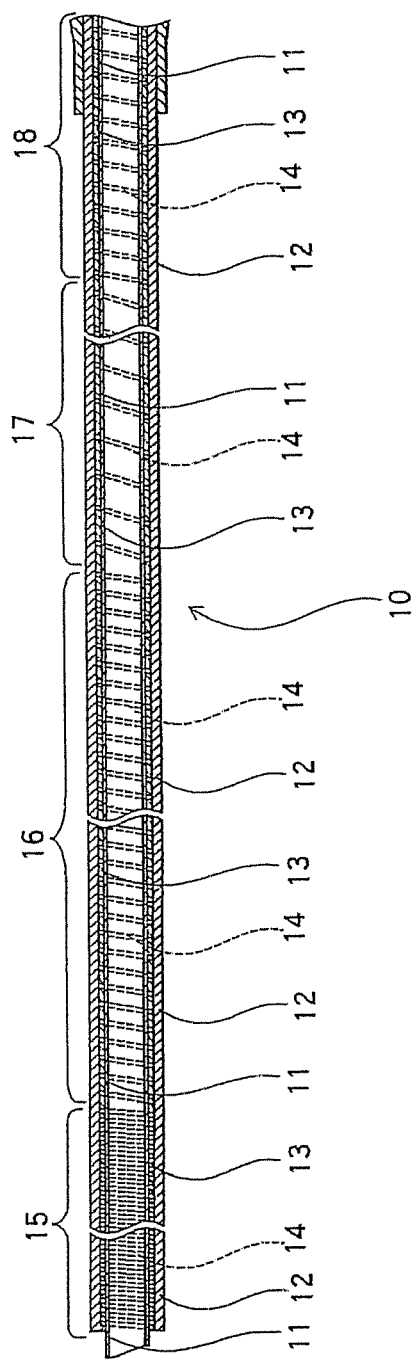
FIG. 3 is a cross-sectional view of a portion of the sheath according to one example.

The intermediate tube 13 includes, as shown in FIG. 3, the spiral shaped slit 14 which is continuous from the distal portion to the proximal portion. The spiral shaped slit 14 includes the distal slit portion 15 having the greatest slit density, a first middle slit portion 16 which is continuous with the distal slit portion 15 and which also has a lower slit density than the distal slit portion 15, a second middle slit portion 17 which is continuous with the first middle slit portion 16 and which also has a lower slit density than the first middle slit portion 16, and a proximal slit portion 18 which is continuous with the second middle slit portion 17 and which has a greater slit density than the second middle slit portion 17. It should be noted that it is preferable to provide both the first middle slit portion 16 and the second middle slit portion 17 as the middle slit portion, though it is also possible to employ only one middle slit portion.

It is preferable for the slit density of the proximal slit portion 18 to be 5/4 to 5/2 times as much as the slit density of the second middle slit portion 17, more preferably 5/4 to 5/3 times. Also, it is preferable for the length of the proximal slit portion to be 20 mm to 100 mm. The slit density refers to the total surface area of the slit portion which exists in a predetermined unit length of the portion of the tube in the axial direction of the intermediate tube 13.

With respect to the sheath tube 10 shown in FIG. 3, the slit density of the intermediate tube 13 is adjusted varied by the length of the slit pitch (i.e., the distance between adjacent slits) so that the greater (longer) the slit pitch, the lower the slit density. Specifically, the intermediate tube 13 is constructed such that the slit pitch of the distal slit portion 15 is the shortest, the first middle slit portion 16 has a slit pitch longer than that of the distal slit portion 15, and the second middle slit portion 17 has a slit pitch further greater (longer) than that of the first middle slit portion 16. The proximal slit portion 18 has a shorter slit pitch than that of the second middle slit portion 17. For this reason, the sheath tube 10 is constructed such that the stiffness of the sheath tube becomes gradually higher (i.e., gradually increases) from the distal tip toward the proximal side, and at the same time there is presented a little bit of flexibility at the proximal portion of the sheath tube.

It is preferable for the slit pitch of the distal slit portion 15 to be 0.3 mm to 1.0 mm, more preferably 0.5 mm to 0.8 mm. Also, it is preferable for the length of the distal slit portion 15 to be 10 mm to 100 mm, more preferably 20 mm to 50 mm.

The slit pitch of the first middle slit portion 16 is preferably 1.0 mm to 5.0 mm, more preferably 1.0 mm to 2.0 mm. The slit pitch of the first middle slit portion 16 is preferably 2 to 4 times greater than the slit pitch of the distal slit portion 15. Also, it is preferable for the length of the first middle slit portion 16 to be 50 mm to 250 mm, more preferably 150 mm to 250 mm.

The slit pitch of the second middle slit portion 17 is preferably 3 mm to 6 mm, more preferably 4 mm to 5 mm. It is also preferable for the slit pitch of the second middle slit portion 17 to be 5/4 to 5/2 times greater than the slit pitch of the proximal slit portion 18, more preferably 5/4 to 5/3 times. Also, it is preferable for the slit pitch of the second middle slit portion 17 to be 2 to 4 times greater than the slit pitch of the first middle slit portion 16. Additionally, the length of the second middle slit portion 17 is preferably 500 mm to 900 mm, more preferably 600 mm to 800 mm.

The slit pitch of the proximal slit portion 18 is preferably 2 mm to 4 mm, more preferably 3 mm to 3.5 mm. It is also preferable for the slit pitch of the proximal slit portion 18 to be 2/5 to 4/5 times greater than the slit pitch of the second middle slit portion 17, more preferably 3/5 to 4/5 times.

In the disclosed embodiment, the slit pitch in each of the slit portions is preferably constant, meaning that the slit pitch throughout the length of the distal slit portion is constant, the slit pitch throughout the length of the proximal slit portion is constant, etc. However, it is also possible for one, some or all of the slit portions mentioned above to have slit pitches that change gradually.

The intermediate tube 13 preferably includes a slit density transition portion of a predetermined length between the second middle slit portion 17 and the proximal slit portion 18 in which the slit density becomes gradually higher (the slit density gradually increases), specifically the slit pitch becomes gradually short, toward the proximal direction. Similarly, it is preferable for the intermediate tube 13 to include a slit density transition portion of a predetermined length between the distal slit portion 15 and the first middle slit portion 16 in which the slit density becomes gradually lower (the slit density gradually decreases), specifically the slit pitch becomes gradually longer, toward the proximal direction. Similarly, it is preferable for the intermediate tube 13 to include a slit density transition portion of a predetermined length between the first middle slit portion 16 and the second middle slit portion 17 in which the slit density becomes gradually lower (the slit density gradually decreases), specifically the slit pitch becomes gradually longer toward the proximal direction. The length of each of these slit density transition portions is preferably 100 mm to 300 mm, more preferably 150 mm to 250 mm.

Figure 4:
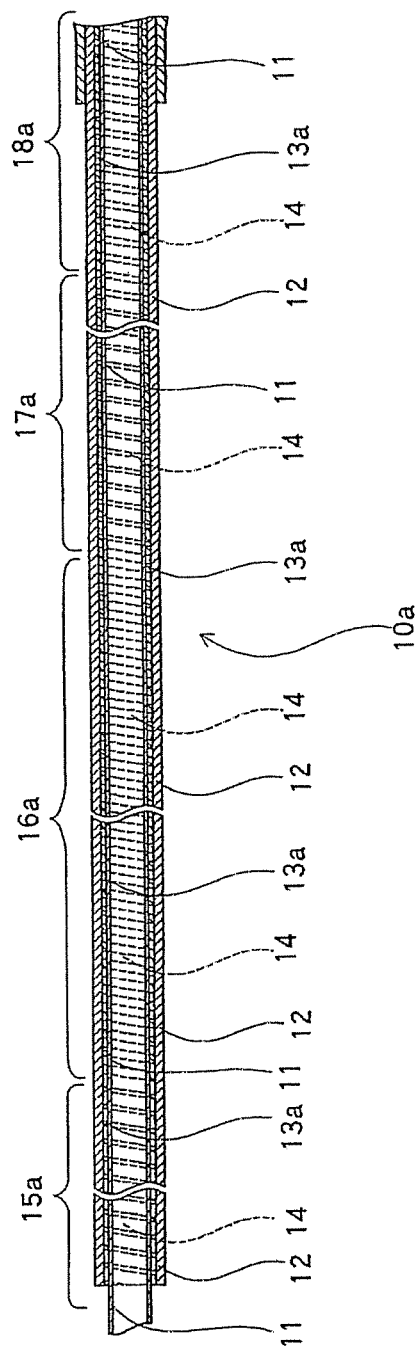
FIG. 4 is a cross-sectional view of a portion of a sheath according to another embodiment.

In addition, it is also possible for the slit density of the slit 14 to be adjusted depending on the slit width such as the sheath tube 10a shown in FIG. 4. The shorter the slit width is, the lower the slit density becomes.

An intermediate tube 13a of this sheath tube 10a, in a manner similar to the intermediate tube 13 mentioned above, includes a spiral-shaped slit 14 which is continuous from the distal portion to the proximal portion. In this intermediate tube 13a, the slit width of a distal slit portion 15a is the widest, a first middle slit portion 16a has a narrower slit width than that of the distal slit portion 15a, and a second middle slit portion 17a has a further narrower slit width that of the first middle slit portion 16a. In addition, a proximal slit portion 18a has a wider (greater) slit width than that of the second middle slit portion 17a. For this reason, the stiffness of the sheath tube 10a becomes gradually higher (the stiffness gradually increases) from the distal tip toward the proximal side, and at the same time the proximal portion exhibits a little bit of flexibility.

It is preferable for the slit width of the distal slit portion 15a to be 0.08 mm to 0.12 mm, more preferably 0.09 mm to 0.11 mm. Also, the length of the distal slit portion 15a is preferably 10 mm to 100 mm, more preferably 20 mm to 50 mm.

The slit width of the first middle slit portion 16a is preferably 0.07 mm to 0.1 mm, more preferably 0.08 mm to 0.09 mm. It is also preferable for the slit width of the distal slit portion 15a to be 5/3 to 5/4 times the slit width of the first middle slit portion 16a. Also, the length of the first middle slit portion 16a is preferably 50 mm to 250 mm, more preferably 150 mm to 250 mm.

It is preferable for the slit width of the second middle slit portion 17a to be 0.06 mm to 0.09 mm, more preferably 0.07 mm to 0.08 mm. Also, the slit width of the second middle slit portion 17a is preferably 9/10 to 6/7 times the slit width of the first middle slit portion 16a. Additionally, the length of the second middle slit portion 17a is preferably 500 mm to 900 mm, more preferably 600 mm to 800 mm.

The slit width of the proximal slit portion 18a is preferably 1.2 to 4 times the slit width of the second middle slit portion 17a, more preferably 1.5 to 3 times. The slit width of the proximal slit portion 18a is preferably 0.07 mm to 0.1 mm.

It is preferable the slit pitch in each of the distal slit portion 15a, the first middle slit portion 16a, the second middle slit portion 17a and the proximal slit portion 18a described above is constant, meaning that the slit pitch throughout the length of the distal slit portion 15a is preferably constant, the slit pitch throughout the length of the first middle slit portion 16a is preferably constant, the slit pitch throughout the length of the second middle slit portion 17a is preferably constant, and the slit pitch throughout the length of the proximal slit portion 18a is preferably constant. However, in this disclosed embodiment, it is possible for one, some or all of the slit portions 15a, 16a, 17a, 18a described above to have slit pitches that change gradually.

In this type of intermediate tube 13a, it is preferable to include a slit density transition portion of a predetermined length between the second middle slit portion 17a and the proximal slit portion 18a in which the slit width becomes gradually wider (the slit width gradually increases) toward the proximal direction. Similarly, it is preferable for the intermediate tube 13a to include a slit density transition portion of a predetermined length between the distal slit portion 15a and the first middle slit portion 16a in which the slit width becomes gradually narrower (the slit width decreases) toward the proximal direction. Similarly, it is preferable for the intermediate tube 13a to include a slit density transition portion of a predetermined length between the first middle slit portion 16a and the second middle slit portion 17a in which the slit width becomes gradually narrow toward the proximal direction. The length of each of the slit density transition portions is preferably 100 mm to 300 mm, more preferably 150 mm to 250 mm.

In addition, it is also possible for the slit density of the slit 14 to be adjusted by changing both the slit pitch (i.e., the distance between axially adjacent portions of the slit) and the slit width (i.e., the width of the slit itself).

The protector 32 is fixed at the proximal tip of the sheath tube 10. Specifically, the proximal portion of the sheath tube 10 is inserted into, or positioned in, the lumen of the protector 32 and fixed relative to the protector.

The protector 32 is fixed at the proximal portion of the sheath tube 10 at which the proximal portion of the proximal slit portion 18 is positioned. In other words, the sheath tube 10 is fixed on the protector 32 at the proximal portion of the proximal slit portion 18 (18a). The sheath tube 10 is constructed such that the proximal slit portion 18 (18a) is positioned in the protector 32 by a predetermined length (i.e., a predetermined length of the proximal slit portion 18 is located in the protector 32). Referring to FIG. 5, the protector 32 includes a distal-most end 32a for kink inhibition which is in close contact with the outer surface of the sheath tube 10 and which has an outer diameter that decreases toward the distal side. It is preferable for the distal portion of the proximal slit portion 18 (18a) to be positioned on the distal side as much as 5 mm to 150 mm from the distal tip of the distal portion 32a for kink inhibition of the protector 32, more preferably 10 mm to 100 mm.

The base portion tube 33 is fixed at the proximal portion of the protector 32. The base portion tube 33 extends toward the proximal side over a predetermined length. It is preferable for the base portion tube 33 to have the same or a little bit longer length than the maximum axial moving distance of the base portion tube 33 in a case in which the shaft for obtaining data is moved to the proximal side during use. It is also preferable for the base portion tube 33 to be transparent by which the inside portion can be visibly confirmed.

The tube hub 34 is fixed at the proximal portion of the base portion tube 33. The tube hub 34 is composed of a distal side member 34a and a proximal side member 34b. The proximal portion of the base portion tube 33 intrudes into and is bonded to the inside portion of the proximal side member 34b. Further, a seal member is housed in the proximal inside portion of the tube hub 34 (specifically, in the inside portion of the proximal side member 34b). The seal member 36 is slidable on an outer tube of the operation member 4 in a substantially liquid-tight manner, and this seal member is fixed at the tube hub 34 by a cap member 35.

Figure 6:
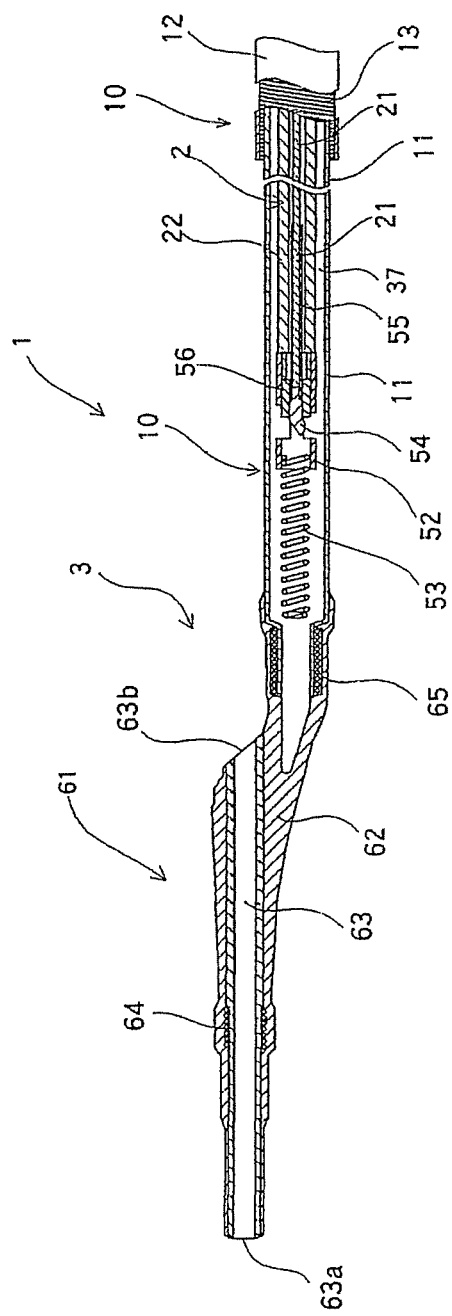
FIG. 6 is an enlarged cross-sectional view of a distal portion of one embodiment of the probe for insertion into a living body, as applied to an optical probe for insertion into a living body.

The distal tip of the sheath tube 10 is provided, as shown in FIG. 6, with the distal sheath portion 61. The distal sheath portion 61 includes the guide wire lumen 63 possessing a distal opening 63a and a proximal side opening 63b. In particular, in the embodiment shown in FIG. 6, the distal sheath portion 61 includes a distal portion forming member 62, and the guide wire lumen 63 is comprised of a tube body buried in the distal portion forming member 62 for forming the wire lumen in the distal portion forming member 62. Also, the distal sheath portion 61 includes a first contrast portion 64 provided at an intermediate portion of the distal portion forming member 62, more specifically at a position located a little bit on the proximal side from the distal portion of distal portion forming member 62. A second contrast portion 65 is also provided at a position on the proximal end portion of the distal sheath portion 61. The second contrast portion 65 is axially spaced in the proximal direction from the proximal end of the first contrast portion 64, and is on the distal side of the distal tip of the shaft for obtaining data 2.

As shown in FIGS. 1 and 6-9, the shaft for obtaining data 2 includes the optical fiber 21 having the tip portion 54 which passes through the drive-transmission hollow shaft 22 and the inside of the hollow shaft 22 and which is also exposed from the distal portion of the hollow shaft 22, a connector which is connected to the proximal portion of the optical fiber 21, and a connection member 25 which connects the proximal portion of the hollow shaft 22 and the connector. The shaft 2 rotates by a rotation force which is applied by the connector.

The drive-transmission hollow shaft 22 is a hollow body having a predetermined length in which is provided a lumen portion passing-through from the proximal tip to the distal tip. The lumen portion is constructed such that the optical fiber is housable in the lumen. The drive-transmission hollow shaft 22 in this disclosed embodiment includes a shaft in which a coil, a round wire or a flat plate shaped metal is wound in a single layer or multiple layers in a coil shape or in a blade shape, a shaft in which a metal-made and stiffness applying body is coated on or buried in a resin tube or the like. The shaft is preferably a shaft made of a flat plate of stainless steel (SUS304, SUS316 or the like) configured in the manner described.

For the optical fiber 21, it is possible to use a well known solid optical fiber having a predetermined length. For example, it is possible to use a single mode optical fiber for the optical fiber 21. Such an optical fiber is constructed of a core for transmitting the light and a clad which coats the outer surface of the core and which has a refractive index a little bit smaller (less) than that of the core. In this optical fiber, the light is transmitted by repeating total-reflection on the boundary surface between the core and the clad only in a case in which an incidence angle is larger than a critical angle. Also, it is preferable for the outer surface of the clad of the optical fiber to be coated by a resin member which is called a jacket.

As shown in FIG. 6, the distal tip of the optical fiber 21 is optically connected with the tip portion 54. In the probe for insertion into a living body of this embodiment, a lens is used for the tip portion 54. The lens can be a ball lens, a drum lens, a hemispheric lens, a GRIN lens, a half drum lens, a SELFOC® lens or the like. It is preferable that the lens is a ball lens.

Figure 9:
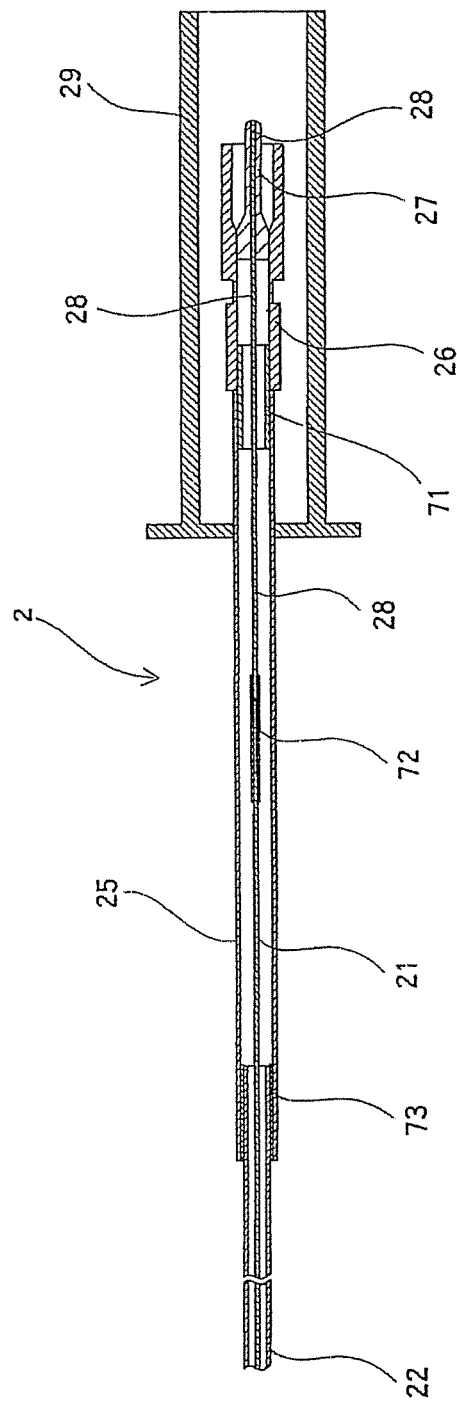
FIG. 9 is an enlarged cross-sectional view of the proximal portion of the shaft for obtaining data shown in FIG. 8.

FIG. 9 illustrates that the proximal tip of the shaft for obtaining data 2 is provided with the connector. Specifically, the proximal portion of the optical fiber 21 is bonded to a proximal side optical fiber 28 in a bonding portion 72. A ferrule 27 is fixed at the proximal portion of the proximal side optical fiber 28. The ferrule 27 is housed in the proximal portion of a stopper 26 and at the same time is fixed at the stopper 26. Consequently, the optical fiber 21 is fixed at the stopper 26 indirectly. The connector is comprised of the stopper 26, the ferrule 27 and a joint portion 29.

Figure 7:
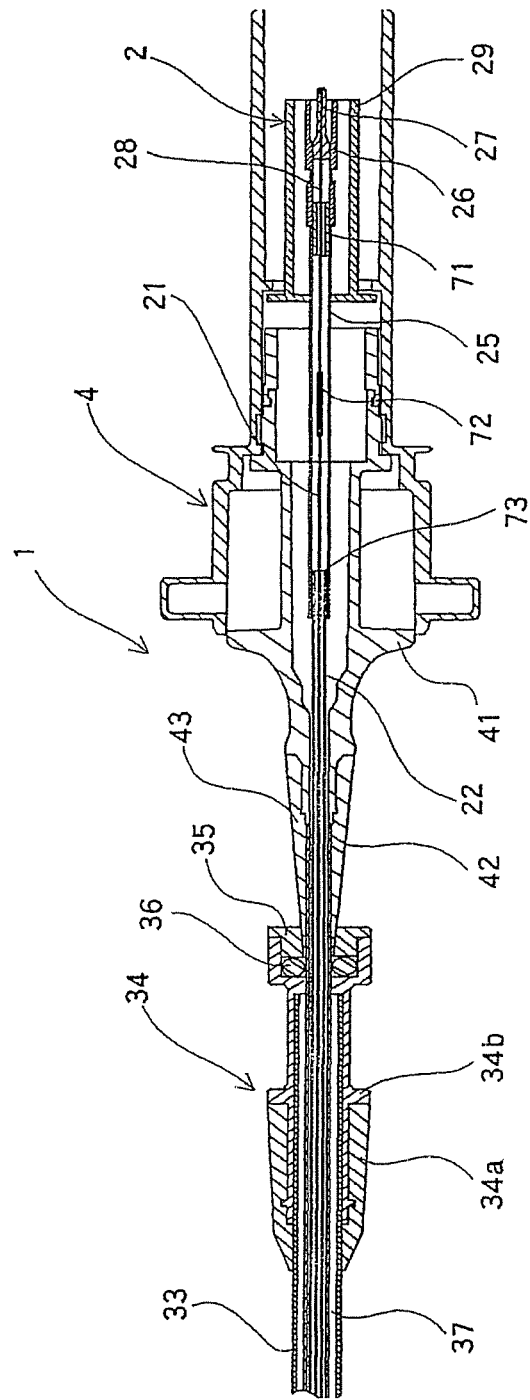
FIG. 7 is an enlarged cross-sectional view of a proximal portion of an embodiment of the probe as applied to the optical probe for insertion into a living body.
Figure 8:
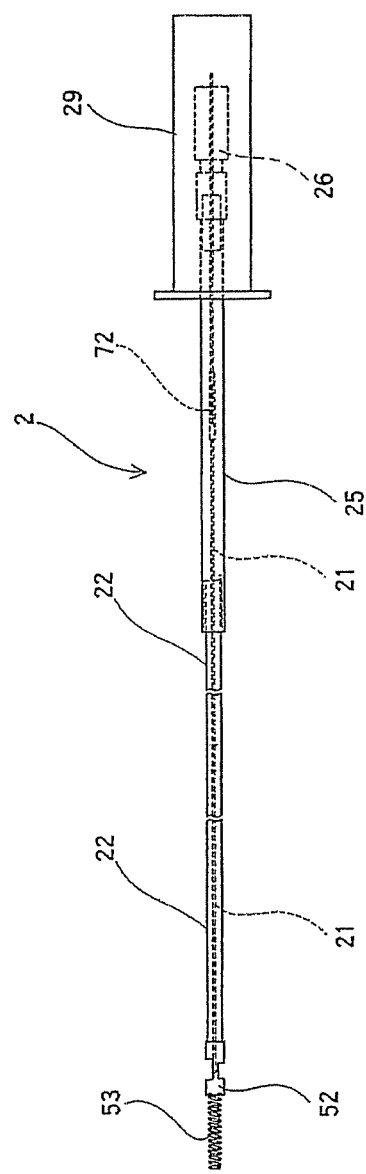
FIG. 8 is a plan view of a shaft for obtaining data in an embodiment of the probe disclosed here, wherein the probe is the optical probe for insertion into a living body.

As illustrated in FIGS. 7-9, the proximal portion of the hollow shaft 22 is fixed at the distal portion of the cylindrical-shaped connection member 25. Specifically, the proximal portion of the hollow shaft 22 is fixed at the connection member 25 through a metal sleeve 73 which wraps around the proximal portion of the hollow shaft 22 and which is also housed in the connection member 25. The proximal portion of the connection member 25 is fixed at the distal portion of the stopper 26. Specifically, the proximal portion of the connection member 25 and the distal tip of the stopper 26 are fixed by a fixation member 71 which intrudes into both the connection member 25 and the stopper 26. Consequently, the hollow shaft 22 is fixed at the stopper 26 indirectly.

Consequently, the shaft for obtaining data, in other words the hollow shaft and the optical fiber, rotate by a rotation force which is applied to the stopper 26. Also, the joint portion 29 is provided at the proximal portion of the shaft for obtaining data 2.

FIG. 6 illustrates a housing 52 for housing the tip portion 54. The housing 52 is fixed at the distal portion of the hollow shaft 22. This housing 52 is a cylindrical body having an opening portion at which is exposed the tip portion 54. The proximal portion of the housing 52 is fixed at the distal portion of the hollow shaft 22 by a fixation member 56. Also, at the proximal portion of the tip portion, there is provided a sleeve 55 which extends a predetermined length toward the proximal side and which wraps around the distal portion of the optical fiber. The tip portion 54 is fixed at the housing 52 through the proximal portion of the housing. Consequently, the distal portion of the optical fiber is fixed at the hollow shaft.

Further, a rotation stabilization member 53 is fixed at the distal portion of the housing 52 for housing the tip portion. The rotation stabilization member 53 extends toward the distal direction. The illustrated example of the rotation stabilization member is a coil body.

The probe for insertion into a living body 1 of this embodiment also includes, as shown in FIGS. 1 and 7, the operation member 4. The operation member 4 includes a distally located outer tube 42 which is approachable into the lumen 37 of the sheath 3 from the proximal portion of the sheath 3. The outer tube 42 has a length that is the same as, or longer than, the moving distance of the shaft 2 during use. The operation member 4 also includes the tube hub 43 at the proximal portion of the outer tube 42 and a holding member 41 for operation fixed at the tube hub 43. The hollow shaft 22 of the shaft for obtaining data 2 passes through the outer tube 42 and extends to the distal side of the sheath 3. Further, the outer tube 42 has the length mentioned above so that it is structured such that the hollow shaft 22 of the shaft for obtaining data 2 is enclosed or surrounded in the outer tube 42 and is not exposed even in a state of being moved by a predetermined length in the axial direction during use.

For the outer tube, a hard, or semi-hard or soft resin tube is suitably used or applied. The holding member for operation 41 of the operation member 4 in this embodiment is a cylindrical body having a predetermined length. The holding member 41 is constructed such that the proximal portion of the shaft 2 is housable in the proximal portion of the holding member 41. In the case of a hard resin tube, the tube can be composed of a fluoric resin of PTFE, ETFE or the like. Also, in the case of a semi-hard resin tube, the tube can be composed of a fluoric resin of polyester (for example, polyethylene terephthalate, polybutylene terephthalate), polyolefin (for example, polyethylene, polypropylene), polyamide or the like. For the soft tube, it is possible to use a synthetic rubber of a urethane rubber, a silicon rubber, a butadiene rubber or the like, soft polyvinyl chloride, polyolefin elastomer, polyester elastomer, polyamide elastomer or the like.

The probe for insertion into a living body 1 of this embodiment is constructed such that the shaft for obtaining data 2 rotates in the inside of the operation member 4. Also, the seal member 36 is housed in the tube hub 34 constituting the proximal portion of the sheath 3, and this seal member contacts the outer tube of the operation member 4 while not contacting the shaft for obtaining data 2. Thus, the rotation of the shaft for obtaining data 2 is not disturbed or inhibited by the seal member 36.

Set forth below is a description of the manner of using the probe for insertion into a living body.

The probe for insertion into a living body 1 is used by connecting the proximal portion (connector portion of the shaft for obtaining data and proximal portion of the holding member for operation of the operation member 4) to an external apparatus.

The external apparatus can be an apparatus which includes a driving source adapted to be coupled or connected to the connector of the shaft 2 for rotating the shaft to obtain high-speed data, a light source for supplying the light to the optical fiber of the shaft 2, and an image display function which executes imaging by using a light received from the tip portion (lens portion) of the shaft for obtaining data 2.

The use of the probe for insertion into a living body of the present invention involves inserting the probe for insertion into a living body 1 in an aimed (target) coelom. The proximal portion of the probe 1 is then connected to an external apparatus. This can be done once the probe is positioned at the desired location. When the external drive apparatus is driven, the driving torque is transmitted to the hollow shaft through the connector, and the shaft 2 rotates. In association with that rotation of the shaft 2, the tip portion 54 also rotates. Then, in the case of executing an axial direction scan depending on the probe, the holding member 41 of the operation member 4 is grasped and moved in the proximal direction. Thus, as can be seen from a comparison of FIG. 10 and FIG. 11, the shaft for obtaining data 2 is moved in the proximal direction together with the operation member 4 and reaches a state of being pulled out by a predetermined distance from the sheath 3, and the proximal side portion of the shaft for obtaining data is in a non-housing state with respect to the sheath by an amount represented by the moving distance.

The description below is a description of a probe for insertion into a living body according to another embodiment.

Figure 10:
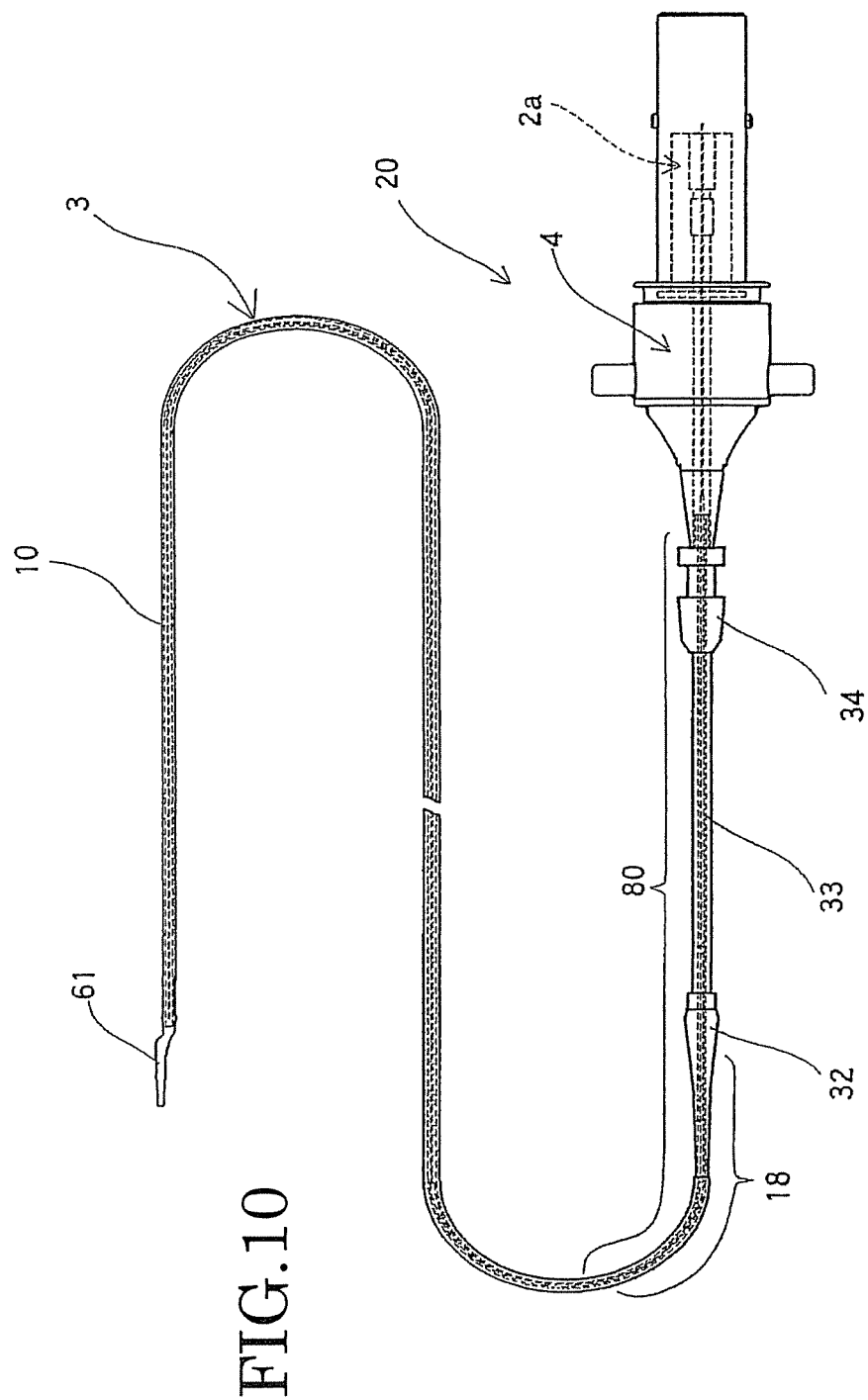
FIG. 10 is a plan view of another embodiment of the probe for insertion into a living body, wherein the probe is an optical probe for insertion into a living body.
Figure 11:
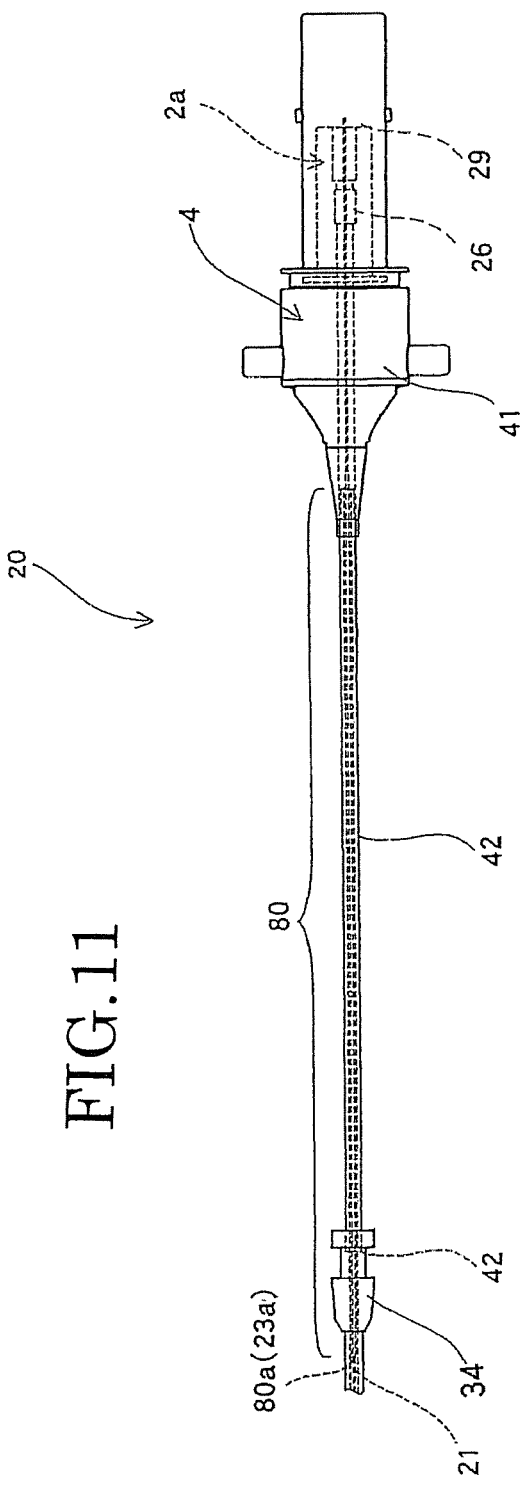
FIG. 11 is a plan view of a probe explaining operation of the probe for insertion into a living body shown in FIG. 10.
Figure 12:
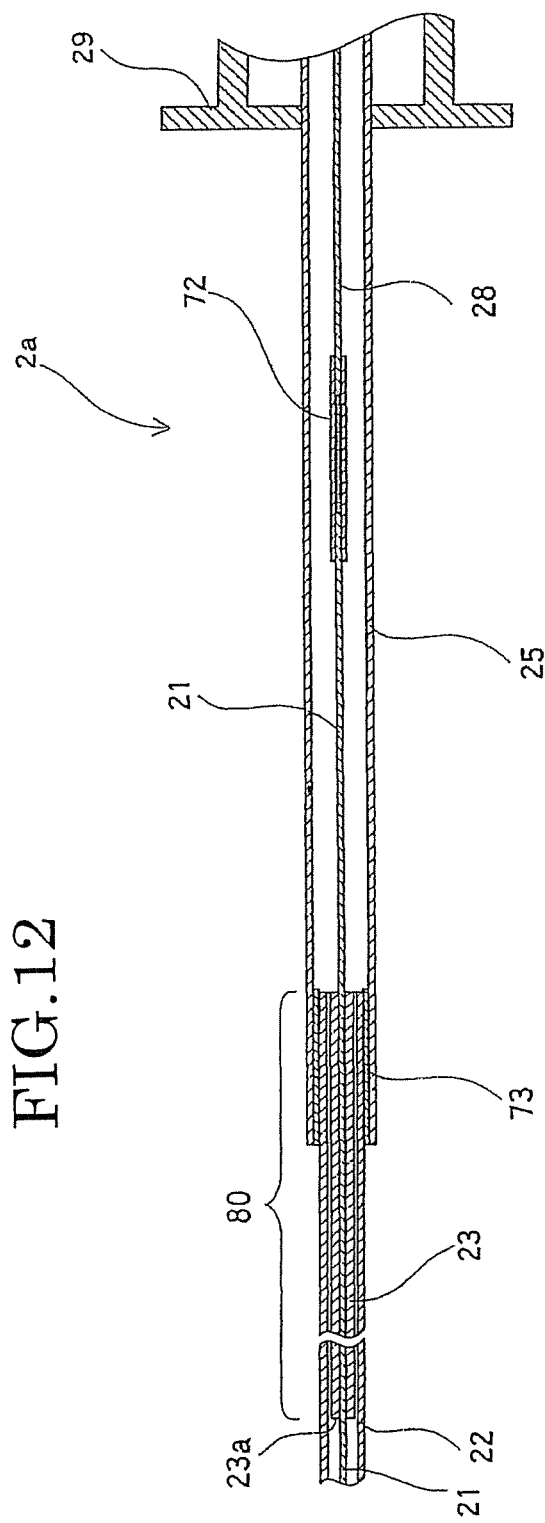
FIG. 12 is an enlarged cross-sectional view of a proximal tip portion of the shaft for obtaining data used for the probe for insertion into a living body shown in FIG. 10.

This embodiment of the probe is illustrated in FIGS. 10-12. The probe for insertion into a living body is applied to an optical probe for insertion into a living body.

The following description focuses primarily on difference between this embodiment and the embodiment described above. Features in this second embodiment that are the same as in the earlier embodiment are designated by common reference numerals and a detailed description of such features is not repeated. The difference between the probe for insertion into a living body 20 of this embodiment and the probe for insertion into a living body 1 discussed above is that there is included in this second embodiment a differently constructed shaft for obtaining data 2a. The sheath 3 and the operation member 4 have constructions that are the same as that described above.

The shaft for obtaining data 2a in this embodiment is movable in the axial direction a predetermined length when used. The shaft for obtaining data 2 includes a vibration repression portion 80 which has the same or longer length than the moving distance of the shaft 2a from the vicinity of the proximal portion of the hollow shaft 22. The vibration repression portion 80 also represses vibration when rotating the shaft for obtaining data in which the distal tip is positioned on the distal side from the distal portion of the proximal slit portion 18.

The probe for insertion into a living body 20 of this embodiment is a so-called linearly scannable probe for insertion into a living body and for this reason, when used, the shaft for obtaining data 2a is moved in the axial direction backward (in the proximal direction) a predetermined length with respect to the sheath. As indicated, the length of the vibration repression portion 80 is the same as or longer (greater) than the moving distance of the shaft for obtaining data 2a from the vicinity of the proximal portion of the hollow shaft 22. The vibration repression portion 80 of the shaft 2a is provided with a length which presents a state in which the distal tip of the shaft 2a remains housed in the sheath on an occasion when the shaft 2a, during use, is moved in the proximal direction by the maximum amount. In other words, the vibration repression portion 80 has a length such that the distal tip 80a of the vibration repression portion 80 never reaches a state of sheath non-housing (i.e., a state where the distal tip 80a is not housed in or covered by the sheath 3) even on an occasion when the shaft for obtaining data 2a is moved to the proximal side by the maximum amount. It is suitable for the length of the vibration repression portion to be 20 cm to 40 cm. It is possible for the vibration repression portion to be composed of a vibration repression reinforcement portion, a vibration absorption repression portion or the like. Preferably, it is a vibration repression reinforcement portion. Further, as shown in FIG. 10, the probe is constructed such that the distal tip of the vibration repression portion 80 is positioned on the distal side from the distal tip of the proximal slit portion 18 in a state in which the distal portion of the operation member 4 is attached and in contact with the tube hub 34 of the sheath 3. For this reason, the vibration repression portion 80 is constructed as a reinforcement for the proximal slit portion of the sheath 3.

FIG. 12 illustrates that in this embodiment of the probe for insertion into a living body, the vibration repression portion 80 is constituted by a reinforcement tube 23 which wraps around (i.e., circumferentially encircles or surrounds) the optical fiber 21 in the hollow shaft 22 and forms the vibration repression reinforcement portion. The reinforcement tube 23 is positioned in the vicinity of the proximal tip of the proximal side hollow shaft 22 and forms a tube extending by a predetermined length toward the distal side. As shown in FIG. 11, the reinforcement tube 23 possesses a length such that the distal tip 23a of the reinforcement tube 23 is housed in the sheath in a maximum moving state of the shaft 2a in the proximal direction. In other words, as mentioned above, the reinforcement tube 23 has a length such that the distal tip 23a of the tube 23 never reaches a non-housing or non-covered state, even when the shaft 2a is moved in the proximal direction by the maximum amount. It is suitable for the length of the reinforcement tube 23 to be 20 cm to 40 cm.

As illustrated in FIG. 12, the reinforcement tube 23 of the probe for insertion into a living body 20 of this embodiment is sized and configured so that the inner surface of the reinforcement tube 23 closely contacts and wraps around the optical fiber 21. At the same time, the reinforcement tube 23 forms a tube whose outer diameter is a little bit smaller than the inner diameter of the hollow shaft 22. For this reason, the reinforcement tube 23 and the hollow shaft 22 are sized and configured such that a gap exists between the outer surface of the reinforcement tube 23 and the inner surface of the hollow shaft 22. It is also possible for the reinforcement tube to be sized and configured such that it substantially contacts the inner surface of the hollow shaft, with substantially no gap between the outer surface of the reinforcement tube 23 and the inner surface of the hollow shaft 22.

In addition, it is also possible for the reinforcement tube to be constructed such it wraps around (i.e., circumferentially encircles or surrounds) the optical fiber 21 without closely contacting the optical fiber 21, while at the same time being fixed on (tightly contacting) the inner surface of the hollow shaft 22. In the shaft for obtaining data of this example, a gap exists between the outer surface of the optical fiber 21 and the inner surface of the reinforcement tube 23.

The reinforcement tube is preferably a resin-made tube, a fiber-made tube, a metal tube or the like. Examples of the resin-made tube include a hard tube, a semi-hard tube and a soft tube. It is possible for the hard tube to be a tube composed of a fluoric resin of PTFE, ETFE or the like. For the semi-hard tube, it is possible to employ a tube composed of a fluoric resin of polyester (for example, polyethylene terephthalate, polybutylene terephthalate), polyolefin (for example, polyethylene, polypropylene), polyamide or the like. Examples of materials for the soft tube include a synthetic rubber of an urethane rubber, a silicon rubber, a butadiene rubber or the like, soft polyvinyl chloride, polyolefin elastomer, polyester elastomer, polyamide elastomer or the like.

In addition, it is also possible for the vibration repression portion 80 to be constituted by a high strength portion of the optical fiber 21. As an example, the high strength portion can be formed by a large-diameter portion of the optical fiber. With respect to the optical fiber large-diameter portion, it is preferable that a gap exists between the outer surface of the optical fiber large-diameter portion and the inner surface of the hollow shaft 22. It is preferable for the high strength portion to be constituted by the large-diameter portion as mentioned above, but it is also possible for the high strength portion to be constituted in other ways. Further, it is also possible for the high strength portion to be the large-diameter portion as described above and at the same time to be constituted by an optical fiber which is harder than other portions of the optical fiber.

In addition, it is also possible for the vibration repression portion to be formed by injecting a curing filler into a space between the outer surface of the optical fiber 21 and the inner surface of the hollow shaft 22. For the curing filler, it is possible to use a curing filler of a silicon-based resin, a polyurethane-based resin, an epoxy-based resin or the like. Examples of the silicon-based resin curing filler include a silicon-gel, a silicon rubber or the like, and it is suitable for the silicon rubber to be an RTV silicon rubber, an LTV silicon rubber or the like which has adhesion properties. In the case of using a material for the curing filler which also presents flexibility to some extent after curing, the vibration repression portion will constitute the vibration absorption repression portion.

Another embodiment of the probe for insertion into a living body will now be described.

Figure 13:
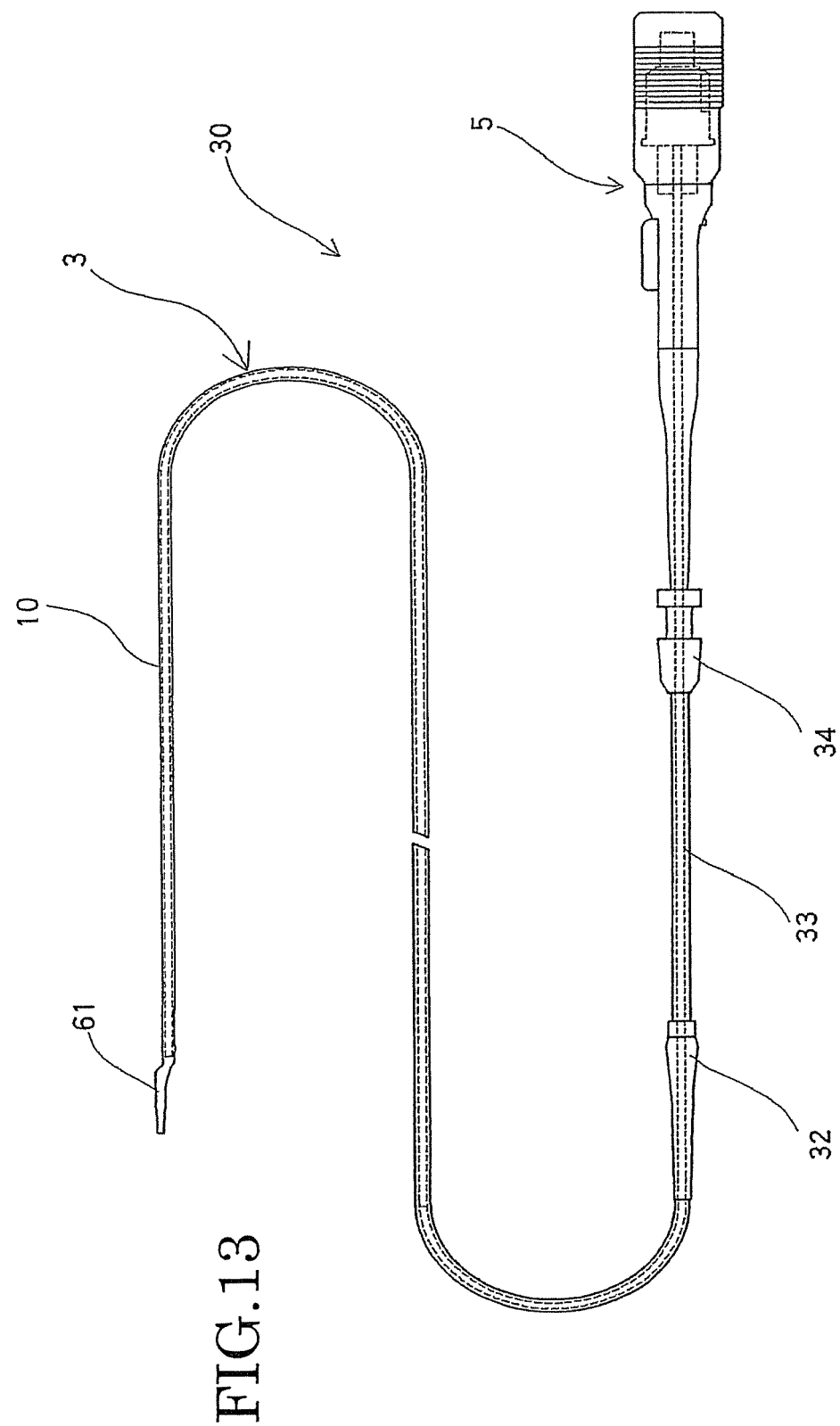
FIG. 13 is a plan view of an embodiment of the probe in which the probe for insertion into a living body is applied to an ultra sound probe for insertion into a living body.
Figure 14:
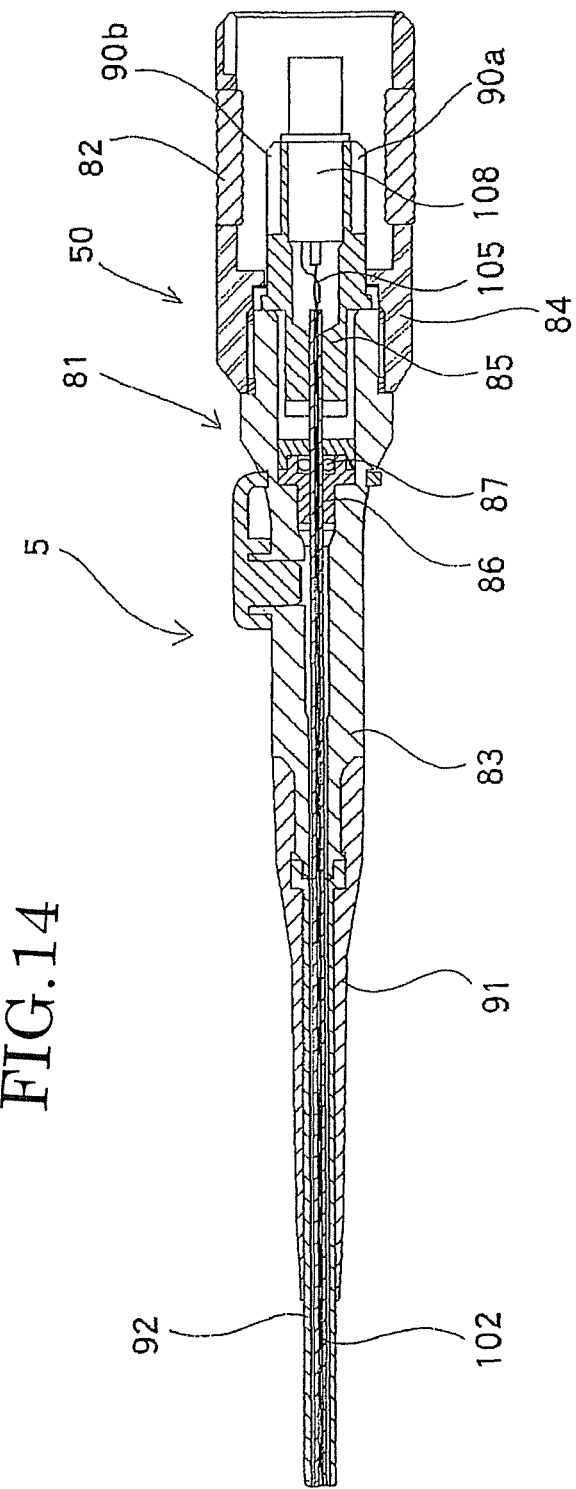
FIG. 14 is an enlarged cross-sectional view of the proximal portion of the probe for insertion into a living body shown in FIG. 13.
Figure 15:
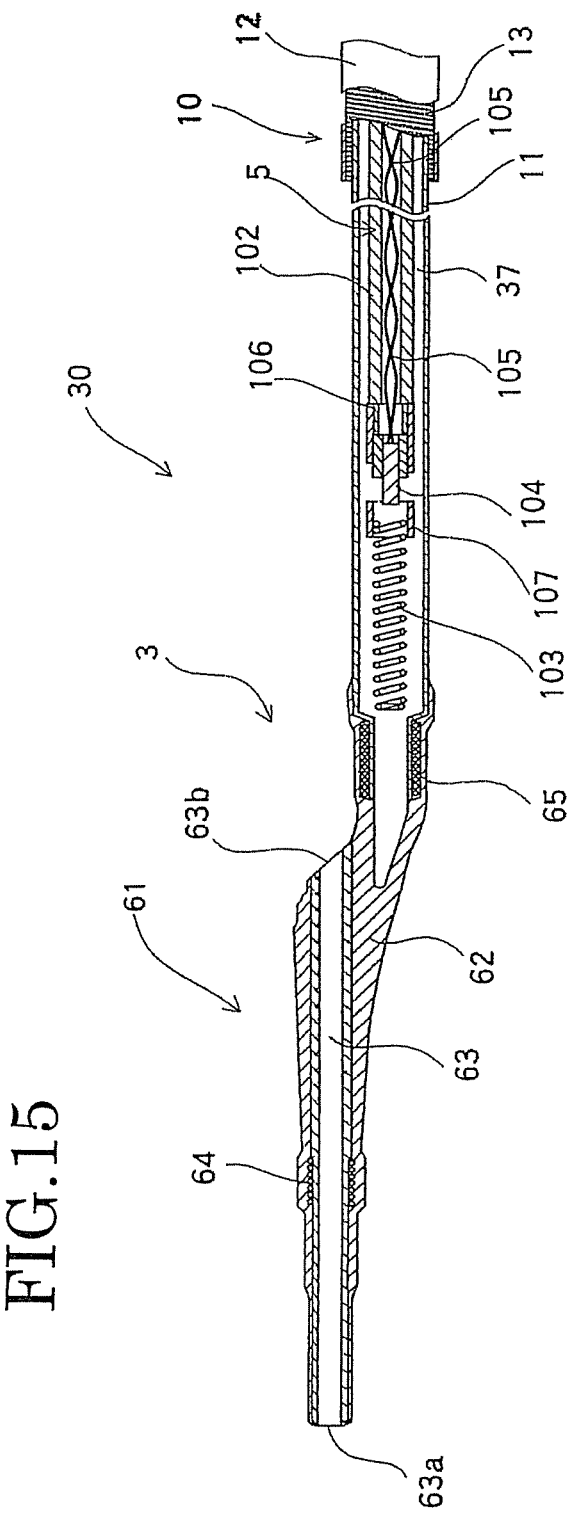
FIG. 15 is an enlarged cross-sectional view of the distal portion of the probe for insertion into a living body shown in FIG. 13.

This embodiment of the probe is illustrated in FIGS. 13-15. The probe here is applied to an ultra sound probe for insertion into a living body.

The probe for insertion into a living body 30 of this embodiment is a probe in which the probe for insertion into a living body of the present invention is applied to an ultra sound probe for insertion into a living body.

The ultra sound probe for insertion into a living body 30 of this embodiment is composed of the sheath 3 which is to be inserted into the coelom and a shaft for obtaining data 5 which is inserted into the sheath 3. The construction of the sheath 3 is the same as that described above.

The shaft for obtaining data 5 in this embodiment includes a drive-transmission hollow shaft 102, an ultrasonic transducer 104 which is fixed at a distal portion of the hollow shaft 102, and a connector 50 connectable with a connection portion of an external drive apparatus. The shaft for obtaining data 5 rotates by a rotation force which is applied by the connector 50.

As illustrated in FIG. 15, the shaft for obtaining data 5 includes, as the tip portion, a transducer 104 having an ultrasonic transducer function for transmitting and receiving ultra sound waves. The distal portion of the shaft for obtaining data 5 is provided with a transducer housing 107 in which the transducer 104 is housed. The housing 107 is a cylindrical body having an opening portion for exposing the transducer 104, and the proximal portion of the housing 107 is fixed at the distal portion of the hollow shaft 102. A rotation stabilization member 103 which extends in the distal direction is attached on the distal portion of the housing 107. In the illustrated embodiment, the rotation stabilization member is in the form of a coil body.

The drive-transmission hollow shaft 102 is a hollow body of a predetermined length having a lumen portion passing-through from the proximal tip to the distal tip. For the drive-transmission hollow shaft 102, there is used a shaft in which a coil, a round wire or a flat plate shaped metal is wound by a single layer or by multi layers in a coil shape or in a blade shape, a shaft in which a metal-made and stiffness applying body is coated on or buried in a resin tube or the like. Specifically, it is preferable for the drive-transmission hollow shaft 102 to be a shaft in which a flat plate of a stainless steel (SUS304, SUS316 or the like) or the like is wound in two layered two-stripes. Also, it is preferable for the hollow shaft 102 to have a breaking strength of 0.4 Kgf or more.

As illustrated in FIG. 15, a signal line 105 is equipped in the inside of the hollow shaft 102. The signal line 105 includes two pieces of lead lines that are twisted, and the distal tip of the signal line 105 is connected to a vibrator of the transducer 104. Also, as shown in FIG. 14, the rear end of the signal line 105 is connected to a receptacle 108 of the connector 50.

The connector 50 shown in FIG. 14 includes a connector housing 81 and a ring-shaped elastic member 82 provided on the outer surface of the housing 81. The elastic member 82 is an annular body having a predetermined width and is fitted in a ring-shaped groove of the predetermined width formed on the outer surface of the connector housing 81 so as not to move easily.

The connector housing 81 is composed of a housing main body portion 83 and a joint portion 84 which is fixed at the rear end of the housing main body portion 83. A rotor 85 is housed in the housing 81, and the receptacle 108 is positioned in the rotor 85. Also, a seal member 86 which includes an O-ring 87 in the inside thereof is housed in the housing main body 83. The proximal portion of the hollow shaft 102 is fixed at the rotor 85. Two grooves 90*a*, 90*b* are provided on the outer surface of the rotor 85. The grooves 90*a*, 90*b* extend in the axial direction. These grooves 90*a*, 90*b* engage the two protrusions of a rotator of an external drive apparatus. Thus, the rotor 85 rotates by a rotation force which is applied to the rotator of the external drive apparatus, and the rotation of the rotor 85 is transmitted to the hollow shaft 102. Also, the signal line 105 is electrically connected to the external drive apparatus through the receptacle 108. An outer tube 92 is fixed at the distal portion of the housing main body 83 by a fixation member 91. The hollow shaft 102 passes through the outer tube 92 and extends in the distal direction of the sheath 3. Further, the outer tube 92 has a length such that the hollow shaft 102 of the shaft for obtaining data 5 is circumferentially covered or surrounded by the outer tube 92 and is not exposed even in a state of being moved to the axial direction by a predetermined length when used. For the outer tube 92, it is possible to suitably use the tube explained above for the outer tube 42.

The probe for insertion into a living body 30 of this embodiment is constructed such that the shaft for obtaining data 5 will rotate. Also, the seal member 36 is housed in the tube hub 34 constituting the proximal portion of the sheath 3. This seal member is a member which contacts the outer tube 92 of the shaft for obtaining data 5, but does not contact the rotating hollow shaft 102 and so the rotation of the shaft for obtaining data is not disturbed.

The external drive apparatus connected to the probe for insertion into a living body 30 is operationally capable of picking-up a signal transmitted from a driving source including a motor and a probe. The external drive apparatus is further connected electrically to a transmitting and receiving circuit and a console having an image display device and the like.

Set forth next is a description of the manner of using the probe for insertion into a living body of this embodiment.

The probe for insertion into a living body 30 is used by connecting a proximal portion (connector of the shaft for obtaining data) to an external apparatus.

An example of the external apparatus includes an apparatus having a driving source which is coupled to the connector of the probe and which is provided for rotating the probe in a high-speed manner, a signal generation device for applying the ultra sound waves to the ultrasonic transducer, and an image display function which executes imaging by using a signal received from the ultrasonic transducer.

In case of using the probe for insertion into a living body as described here, the probe 30 is inserted in an aimed or targeted coelom and positioned therein. Then, the proximal portion of the probe 30 is connected to an external apparatus. When an external drive apparatus is driven, the driving torque is transmitted to the hollow shaft through the connector, the shaft for obtaining data rotates and in association therewith, the transducer also rotates. Then, when executing an axial direction scan depending on the probe, the proximal portion of the shaft for obtaining data is grasped and moved to the proximal side or in the proximal direction. Thus, in a manner similar to that understood from a comparison of FIG. 10 and FIG. 11, the shaft for obtaining data is moved in the proximal direction and reaches a state of being pulled out by a predetermined distance from the sheath, and the proximal side portion of the shaft for obtaining data is in a non-housing state with respect to the sheath by an amount equal to the moving distance.

Having described preferred embodiments of the probe disclosed here with reference to the accompanying drawings, it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A probe for insertion into a living body through a guiding catheter comprising:
 a sheath configured to be positioned in a living body, the sheath possessing a sheath lumen and a distal end portion;
 a shaft movably positioned in the sheath lumen, the shaft comprising a distal end and a shaft lumen;
 a fiber positioned in the shaft lumen and connected to a distal tip device configured to obtain data concerning the living body;
 the sheath including an inside tube, an intermediate tube and an outside tube, the outside tube being positioned radially outwardly of the intermediate tube and radially outwardly of the inside tube, the intermediate tube being positioned radially between the inside tube and the outside tube;
 the inside tube, the intermediate tube and the outside tube each possessing a distal tip, the distal tip of the inside tube extending distally beyond the distal tip of the intermediate tube and the distal tip of the outside tube so that the distal end portion of the sheath is constituted by the inside tube;
 the intermediate tube being comprised of at least one layer that is either a resin layer or a metal layer;
 the at least one layer of the intermediate tube comprising a spiral-shaped slit extending from a distal portion of the at least one layer to a proximal portion of the at least one layer; and
 the spiral-shaped slit comprising a distal slit portion, a first middle slit portion proximal of the distal slit portion, a second middle slit portion proximal of the first middle slit portion and a proximal slit portion proximal of the second middle slit portion, the proximal slit portion being the proximal-most portion of the spiral-shaped slit;
 the distal slit portion possessing a proximal end, the first middle slit portion possessing a proximal end and a distal end, the second middle slit portion possessing a proximal end and a distal end, and the proximal slit portion possessing a distal end, the proximal end of the distal slit portion being directly connected to the distal end of the first middle slit portion, the proximal end of the first middle slit portion being directly connected to the distal end of the second middle slit portion, and the distal end of the proximal slit portion being directly connected to the proximal end of the second middle slit portion;
 the distal slit portion, the first middle slit portion, the second middle slit portion and the proximal slit portion each possessing a slit density;
 the slit density of the entire distal slit portion being different from the slit density of the entire proximal slit portion;
 the slit density of the distal slit portion being greater than the slit density of the first middle slit portion, the slit density of the distal slit portion being greater than the slit density of the second middle slit portion, and the slit density of the distal slit portion being greater than the slit density of the proximal slit portion;
 the first middle slit portion possessing a slit pitch that is 2 to 4 times greater than a slit pitch of the distal slit portion;
 the second middle slit portion possessing a slit pitch that is 5/4 to 5/3 times greater than a slit pitch of the proximal slit portion; and
 the slit density of the proximal slit portion being greater than the slit density of the second middle slit portion.

2. The probe for insertion into a living body according to claim 1, wherein the slit density of the second middle slit portion being is lower than the slit density of the first middle slit portion.

3. The probe for insertion into a living body according to claim 2, wherein the slit density of the proximal slit portion is 5/4 to 5/2 times the slit density of the second middle slit portion.

4. A probe for insertion into a living body through a guiding catheter comprising:
 a sheath sized to be positioned in a living body and possessing a distal end portion;
 a shaft for obtaining data positioned in the sheath;
 the shaft possessing a distal portion configured to obtain diagnostic data;
 the sheath including an inside tube, an intermediate tube and an outside tube, the outside tube being positioned radially outwardly of the intermediate tube and radially outwardly of the inside tube, the intermediate tube being positioned radially between the inside tube and the outside tube;

the inside tube, the intermediate tube and the outside tube each possessing a distal tip, the distal tip of the inside tube extending distally beyond the distal tip of the intermediate tube and the distal tip of the outside tube so that the distal end portion of the sheath is constituted by the inside tube;

the intermediate tube comprising a spiral-shaped slit extending continuously from a distal portion of the shaft to a proximal portion of the shaft; and the spiral-shaped slit comprising a distal slit portion, a middle slit portion and a proximal slit portion, the proximal slit portion being the proximal-most portion of the spiral-shaped slit;

the distal slit portion, the middle slit portion and the proximal slit portion each possessing a slit density;

the slit density of the distal slit portion being greater than the slit density of the middle slit portion and greater than the slit density of the proximal slit portion;

the middle slit portion being continuous with the distal slit portion, and the proximal slit portion being continuous with the middle slit portion;

the slit density of the proximal slit portion being greater than the slit density of the middle slit portion;

the middle slit portion comprising a first middle slit portion and a second middle slit portion;

the distal slit portion possessing a proximal end, the first middle slit portion possessing a proximal end and a distal end, the second middle slit portion possessing a proximal end and a distal end, and the proximal slit portion possessing a distal end;

the proximal end of the distal slit portion being directly connected to the distal end of the first middle slit portion, the proximal end of the first middle slit portion being directly connected to the distal end of the second middle slit portion, and the distal end of the proximal slit portion being directly connected to the proximal end of the second middle slit portion;

the slit density of the first middle slit portion being lower than the slit density of the distal slit portion, the slit density of the second middle slit portion being lower than the slit density of the first middle slit portion, the slit density of the proximal slit portion being greater than the slit density of the second middle slit portion;

the first middle slit portion possessing a slit pitch that is 2 to 4 times greater than a slit pitch of the distal slit portion; and the second middle slit portion possessing a slit pitch that is 5/4 to 5/3 times greater than a slit pitch of the proximal slit portion.

5. The probe for insertion into a living body according to claim 4, wherein the slit density of the proximal slit portion is 5/4 to 5/2 times the slit density of the second middle slit portion.

6. The probe for insertion into a living body according to claim 4, wherein the proximal slit portion possesses a length of 20 mm to 100 mm.

7. The probe for insertion into a living body according to claim 4, further comprising a kink inhibition member fixed at a proximal portion of the proximal slit portion, the kink inhibition member possessing an outer diameter gradually decreasing toward a distal end of the sheath.

8. The probe for insertion into a living body according to claim 7, wherein the kink inhibition member possesses a distal tip, and the proximal slit portion possesses a distal end, the distal end of the proximal slit portion being distally spaced from distal tip of the kink inhibition member by 10 mm to 100 mm.

9. The probe for insertion into a living body according to claim 4, wherein the sheath comprises a shaft lumen and a guide wire lumen, the guide wire lumen being spaced radially outward of the shaft lumen, the shaft for obtaining data being positioned in the shaft lumen, the guide wire lumen being open at a distal tip of the sheath and extending in a proximal direction from the distal tip of the sheath.

10. The probe for insertion into a living body according to claim 4, wherein the spiral-shaped slit comprises a slit density transition portion between the middle slit portion and the proximal slit portion, the slit density in the slit density transition portion gradually increasing in a proximal direction.

11. The probe for insertion into a living body according to claim 4, wherein the spiral-shaped slit comprises a slit density transition portion between the distal slit portion and the middle slit portion, the slit density in the slit density transition portion gradually decreasing in a proximal direction.

12. The probe for insertion into a living body according to claim 4, wherein the spiral-shaped slit comprises a slit density transition portion between the first middle slit portion and the second middle slit portion, the slit density of the slit density transition portion gradually decreasing in a proximal direction.

13. The probe for insertion into a living body according to claim 4, wherein the spiral-shaped slit possesses a slit pitch length, and the slit density of the proximal slit portion is greater than the slit density of the middle slit portion by virtue of variations in the slit pitch length so that a portion of the spiral-shaped slit possessing a longer slit pitch possesses a smaller slit density.

14. The probe for insertion into a living body according to claim 4, wherein the spiral-shaped slit possesses a slit width, and the slit density of the proximal slit portion is greater than the slit density of the middle slit portion by virtue of variations in the slit width so that a portion of the spiral-shaped slit possessing a smaller slit width possesses a smaller slit density.

15. The probe for insertion into a living body according to claim 4, wherein the spiral-shaped slit possesses a slit pitch length and a slit width, wherein the slit density of the proximal slit portion is greater than the slit density of the middle slit portion by virtue of by variations in slit pitch length and the slit width.

16. The probe for insertion into a living body according to claim 4, wherein the shaft for obtaining data comprises a drive-transmission hollow shaft and a tip portion for obtaining data which passes through the inside of the hollow shaft and also which is exposed from the distal portion of the hollow shaft, the drive-transmission hollow shaft being a rotatable shaft rotated by a rotation force applied at a proximal portion.

17. The probe for insertion into a living body according to claim 4, wherein the shaft for obtaining data comprises a drive-transmission hollow shaft, an optical fiber passing through an inside of the hollow shaft and having a tip portion for obtaining data exposed from the distal portion of the hollow shaft, and a connector connectable with a connection portion of an external drive apparatus, the drive-transmission hollow shaft being a rotatable shaft rotated by a rotation force applied by the connector.

18. The probe for insertion into a living body according to claim 4, wherein the shaft for obtaining data comprises a drive-transmission hollow shaft, an ultrasonic transducer fixed at the distal portion of the hollow shaft for obtaining the data, and a connector connectable with a connection portion of an external drive apparatus, the drive-transmission hollow shaft being a rotatable shaft rotated by a rotation force applied by the connector.

* * * * *